US011013530B2

(12) United States Patent
Zollmann et al.

(10) Patent No.: US 11,013,530 B2
(45) Date of Patent: May 25, 2021

(54) SURFACE FEATURES FOR DEVICE RETENTION

(71) Applicant: Medos International Sarl, Le Locle (CH)

(72) Inventors: Véronique Christine Zollmann, Gebenstorf (CH); Jorg Priewe, Kiel (DE); Barbara Schuldt-Hempe, Bad Bramstedt (DE); Susanne Landgrebe, Suelfeld (DE); Stéphane Gully, Rixheim (FR); Roger Berger, Buren (CH)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/297,498

(22) Filed: Mar. 8, 2019

(65) Prior Publication Data

US 2020/0281579 A1  Sep. 10, 2020

(51) Int. Cl.
*A61B 17/34*  (2006.01)

(52) U.S. Cl.
CPC .... *A61B 17/3421* (2013.01); *A61B 2017/348* (2013.01); *A61B 2017/349* (2013.01);
(Continued)

(58) Field of Classification Search
CPC ................ A61B 17/34; A61B 17/3421; A61B 2017/348; A61B 2017/3482;
(Continued)

(56) References Cited

U.S. PATENT DOCUMENTS 4,331,423 A * 5/1982 Yanney, Jr. ............... A61C 5/35
433/225
4,573,448 A  3/1986 Kambin
(Continued)

FOREIGN PATENT DOCUMENTS

CN  102727309 B  11/2014
DE  9415039 U1  11/1994
(Continued)

OTHER PUBLICATIONS

International Search Report and Written Opinion for Application No. PCT/EP2020/055816, dated Jun. 9, 2020 (17 pages).
(Continued)

*Primary Examiner* — Eric S Gibson
(74) *Attorney, Agent, or Firm* — Nutter McClennen & Fish LLP

(57) ABSTRACT

Surface features for device retention are disclosed herein, e.g., for retaining an access port within a patient during a surgical procedure. The surface features can prevent ejection of the access port from a body of a patient. The surface features can be positioned along the access port and configured to glide along body tissues with minimal friction so as not to hinder travel of the access port in an insertion direction. After insertion of the access port, the surface features can engage with surrounding tissue to increase friction therebetween and to prevent ejection of the access port from the patient. Deployment of the surface features can occur due to friction with the surrounding tissue and/or via activation of the surface features to protrude from the access port. The surface features can include teeth, hooks, scales, fins, bristles, braids, and/or threads for engaging tissue. The surface features can be disengaged from the tissue to enable withdrawal of the access port without damaging the surrounding tissue.

27 Claims, 6 Drawing Sheets

(52) U.S. Cl.
CPC ............... *A61B 2017/3482* (2013.01); *A61B 2017/3484* (2013.01); *A61B 2017/3488* (2013.01)

(58) Field of Classification Search
CPC .... A61B 2017/3484; A61B 2017/3488; A61B 2017/349
See application file for complete search history.

(56) References Cited

U.S. PATENT DOCUMENTS

| | | | |
|---|---|---|---|
| 4,646,738 A | 3/1987 | Trott | |
| 4,678,459 A | 7/1987 | Onik et al. | |
| 4,863,430 A | 9/1989 | Klyce et al. | |
| 4,888,146 A | 12/1989 | Dandeneau | |
| 5,080,662 A | 1/1992 | Paul | |
| 5,195,541 A | 3/1993 | Obenchain | |
| 5,285,795 A | 2/1994 | Ryan et al. | |
| 5,290,249 A | 3/1994 | Foster et al. | |
| 5,395,317 A | 3/1995 | Kambin | |
| 5,439,464 A | 8/1995 | Shapiro | |
| 5,529,580 A | 6/1996 | Kusunoki et al. | |
| 5,540,706 A | 7/1996 | Aust et al. | |
| 5,569,290 A | 10/1996 | McAfee | |
| 5,591,187 A | 1/1997 | Dekel | |
| 5,601,569 A | 2/1997 | Pisharodi | |
| 5,653,690 A * | 8/1997 | Booth | A61M 25/04 604/103.07 |
| 5,662,300 A | 9/1997 | Michelson | |
| 5,688,222 A | 11/1997 | Hluchy et al. | |
| 5,697,913 A | 12/1997 | Sierocuk et al. | |
| 5,730,754 A | 3/1998 | Obenchain | |
| 5,733,242 A | 3/1998 | Rayburn et al. | |
| 5,735,792 A | 4/1998 | Vanden Hoek et al. | |
| 5,817,062 A | 10/1998 | Flom et al. | |
| 5,820,623 A | 10/1998 | Ng | |
| 5,824,002 A | 10/1998 | Gentelia et al. | |
| 5,885,300 A | 3/1999 | Tokuhashi et al. | |
| 5,894,369 A | 4/1999 | Akiba et al. | |
| 5,899,425 A | 5/1999 | Corey, Jr. et al. | |
| 5,954,635 A | 9/1999 | Foley et al. | |
| 6,004,302 A * | 12/1999 | Brierley | A61F 9/00781 604/239 |
| 6,033,105 A | 3/2000 | Barker et al. | |
| 6,053,907 A | 4/2000 | Zirps | |
| 6,063,021 A | 5/2000 | Hossain et al. | |
| 6,110,182 A | 8/2000 | Mowlai-Ashtiani | |
| 6,200,322 B1 | 3/2001 | Branch et al. | |
| 6,234,961 B1 | 5/2001 | Gray | |
| 6,283,966 B1 | 9/2001 | Houfburg | |
| 6,286,179 B1 | 9/2001 | Byrne | |
| 6,296,644 B1 | 10/2001 | Saurat et al. | |
| 6,322,498 B1 | 11/2001 | Gravenstein et al. | |
| 6,354,992 B1 | 3/2002 | Kato | |
| 6,371,968 B1 | 4/2002 | Kogasaka et al. | |
| 6,383,191 B1 | 5/2002 | Zdeblick et al. | |
| 6,432,085 B1 * | 8/2002 | Stellon | A61B 17/3421 604/164.04 |
| 6,447,446 B1 | 9/2002 | Smith et al. | |
| 6,468,289 B1 | 10/2002 | Bonutti | |
| 6,558,407 B1 | 5/2003 | Ivanko et al. | |
| 6,575,899 B1 | 6/2003 | Foley et al. | |
| 6,579,281 B2 | 6/2003 | Palmer et al. | |
| 6,626,830 B1 | 9/2003 | Califiore et al. | |
| 6,648,915 B2 | 11/2003 | Sazy | |
| 6,676,597 B2 | 1/2004 | Guenst et al. | |
| 6,688,564 B2 | 2/2004 | Salvermoser et al. | |
| 6,758,809 B2 | 7/2004 | Briscoe et al. | |
| 6,808,492 B2 * | 10/2004 | Snyder | A61B 17/3421 600/114 |
| 6,808,505 B2 | 10/2004 | Kadan | |
| 6,887,198 B2 | 5/2005 | Phillips et al. | |
| 6,983,930 B1 | 1/2006 | La Mendola et al. | |
| 7,087,058 B2 | 8/2006 | Cragg | |
| 7,104,986 B2 | 9/2006 | Hovda et al. | |
| 7,137,949 B2 | 11/2006 | Scirica et al. | |
| 7,182,731 B2 | 2/2007 | Nguyen et al. | |
| 7,341,556 B2 | 3/2008 | Shalman | |
| 7,434,325 B2 | 10/2008 | Foley et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,771,384 B2 | 8/2010 | Ravo | |
| 7,794,456 B2 | 9/2010 | Sharps et al. | |
| 7,811,251 B2 | 10/2010 | Wenchell et al. | |
| 7,811,303 B2 | 10/2010 | Fallin et al. | |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,062,305 B2 * | 11/2011 | Wenchell | A61B 17/3421 606/108 |
| 8,092,464 B2 | 1/2012 | McKay | |
| 8,096,944 B2 | 1/2012 | Harrel | |
| 8,157,833 B2 * | 4/2012 | Au | A61B 17/34 606/191 |
| 8,202,216 B2 | 6/2012 | Melkent et al. | |
| 8,236,006 B2 | 8/2012 | Hamada | |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,690,764 B2 | 4/2014 | Clark et al. | |
| 8,715,251 B2 | 5/2014 | Johnson et al. | |
| 8,721,536 B2 | 5/2014 | Marino et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |
| 8,894,653 B2 | 11/2014 | Solsberg et al. | |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,605 B2 | 1/2015 | Greenberg | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,131,948 B2 | 9/2015 | Fang et al. | |
| 9,144,374 B2 | 9/2015 | Maurice, Jr. | |
| 9,161,745 B2 | 10/2015 | Dodson | |
| 9,198,674 B2 | 12/2015 | Benson et al. | |
| 9,211,059 B2 | 12/2015 | Drach et al. | |
| 9,216,016 B2 | 12/2015 | Fiechter et al. | |

(56) References Cited

U.S. PATENT DOCUMENTS

| | | |
|---|---|---|
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,597,112 B2 | 3/2017 | Stearns et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,636,142 B2 | 5/2017 | Carter |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,348 B2 * | 7/2017 | Au .................. A61B 17/34 |
| 9,700,378 B2 | 7/2017 | Mowlai-Ashtiani |
| 9,706,905 B2 | 7/2017 | Levy |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0187555 A1 * | 8/2005 | Biedermann ......... A61B 17/864 606/62 |
| 2005/0187570 A1 | 8/2005 | Nguyen et al. |
| 2005/0256458 A1 * | 11/2005 | Howard ................ A61M 25/04 604/174 |
| 2005/0256525 A1 | 11/2005 | Culbert et al. |
| 2006/0206118 A1 | 9/2006 | Kim et al. |
| 2006/0211992 A1 | 9/2006 | Prosek |
| 2006/0212061 A1 * | 9/2006 | Wenchell ........... A61B 17/3421 606/191 |
| 2007/0005089 A1 | 1/2007 | Smith et al. |
| 2007/0038219 A1 * | 2/2007 | Matthis ................ A61B 17/866 623/17.11 |
| 2007/0055259 A1 | 3/2007 | Norton et al. |
| 2007/0106319 A1 * | 5/2007 | Au ........................ A61B 17/34 606/191 |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0224495 A1 | 9/2011 | Carter et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0203261 A1 * | 8/2012 | Au ........................ A61B 17/34 606/185 |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0090527 A1 | 4/2013 | Axon |
| 2013/0103067 A1 | 4/2013 | Fabro et al. |
| 2013/0103103 A1 | 4/2013 | Mire et al. |
| 2013/0116510 A1 | 5/2013 | Lutze et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0025121 A1 | 1/2014 | Foley et al. |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275793 A1 | 9/2014 | Song |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0297882 A1 * | 10/2015 | Barker ................. A61N 1/0558 607/116 |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 * | 7/2016 | Beger ................ A61B 17/0218 |
| 2016/0228280 A1 | 8/2016 | Schuele et al. |
| 2016/0235284 A1 | 8/2016 | Yoshida et al. |

(56) References Cited

U.S. PATENT DOCUMENTS

| | | |
|---|---|---|
| 2016/0279389 A1 | 9/2016 | Rosenberg et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0014155 A1 | 1/2017 | Norton et al. |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0021061 A1 | 1/2018 | Reid |

FOREIGN PATENT DOCUMENTS

| | | |
|---|---|---|
| DE | 29916026 U1 | 11/1999 |
| EP | 0537116 A1 | 4/1993 |
| EP | 0807415 A2 | 11/1997 |
| EP | 1702574 A1 | 9/2006 |
| GB | 2481727 A | 1/2012 |
| WO | 96/29014 A1 | 9/1996 |
| WO | 2001/056490 A1 | 8/2001 |
| WO | 2001/089371 A1 | 11/2001 |
| WO | 2002/002016 A1 | 1/2002 |
| WO | 2004/103430 A2 | 12/2004 |
| WO | 2008/121162 A1 | 10/2008 |
| WO | 2009/033207 A1 | 3/2009 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |
| WO | 2016/131077 A1 | 8/2016 |
| WO | 2016/168673 A1 | 10/2016 |
| WO | 2017/006684 A1 | 1/2017 |
| WO | 2017/015480 A1 | 1/2017 |
| WO | 2017/083648 A1 | 5/2017 |

OTHER PUBLICATIONS

International Search Report and Written Opinion for Application No. PCT/US2015/043554, dated Nov. 19, 2015 (8 pages).

International Search Report and Written Opinion for Application No. PCT/US2015/048485, dated Feb. 9, 2016 (16 pages).

International Search Report and Written Opinion for Application No. PCT/US2015/060978, dated Feb. 15, 2016 (8 pages).

International Search Report and Written Opinion for Application No. PCT/US2016/050022, dated Feb. 1, 2017 (19 pages).

Invitation to Pay Additional Fees for Application No. PCT/US2016/050022, dated Nov. 3, 2016 (2 pages).

Iprenburg, M, "Percutaneous Transforaminal Endoscopic Discectomy: the Thessys Method," in Lewandrowski, K., et al, Minimally Invasive Spinal Fusion Techniques, Summit Communications, 2008 pp. 65-81.

Jung, K., et al., "A hands-free region-of-interest selection interface for solo surgery with a wide-angle endoscope: 3reclinical proof of concept," Surg Endosc, 2017, v. 31, pp. 974-980.

* cited by examiner

SURFACE FEATURES FOR DEVICE RETENTION

FIELD

Surface features for device retention are disclosed herein, e.g., for retaining an access port within a patient during a surgical procedure.

BACKGROUND

Access systems can be used in orthopedic surgery or neurosurgery to enable surgeons to introduce devices and/or instruments into a surgical site of a patient. For example, in spinal surgery, an access system can be implanted in situ to allow dilators, scalpels, and/or bone anchors to be passed to the surgical site to the one or more vertebrae. A typical access system can be advanced into the patient until it reaches the surgical site and secured therein, after which instruments and devices can be passed therethrough. Implantation of the access system, while invasive, can provide a clear path of access to the surgical site while minimizing damage to surrounding tissue that can be caused by operating tools.

Existing access systems can have numerous shortcomings. Muscle tissue, e.g. spine muscle, is very strong and can be prone to resisting advancement of the access system therethrough. Muscle activity can also exert a force that can dislodge or even eject the access system back out of the patient, which can cause slippage of surgical instruments that would damage surrounding tissue and increase time spent in the operating room reinserting the system. Securing the access system to the patient by way of anchors or staples can be overly invasive and hinder frequent repositioning of the system that may be required during surgery. Such modifications can also make removal of the access system difficult and cause excessive tissue damage.

Accordingly, there is a continual need for systems and methods that can discourage ejection and retain access systems within surgical sites while minimizing damage to surrounding tissue.

SUMMARY

Surface features for device retention are disclosed herein, e.g., for retaining an access port within a patient during a surgical procedure. The surface features can prevent ejection of the access port from a body of a patient. The surface features can be positioned along the access port and configured to glide along body tissues with minimal friction so as not to hinder travel of the access port in an insertion direction. After insertion of the access port, the surface features can engage with surrounding tissue to increase friction therebetween and to prevent ejection of the access port from the patient. Deployment of the surface features can occur due to friction with the surrounding tissue and/or via activation of the surface features to protrude from the access port. The surface features can include teeth, hooks, scales, fins, bristles, braids, and/or threads for engaging tissue. The surface features can be disengaged from the tissue to enable withdrawal of the access port without damaging the surrounding tissue.

In one aspect, a surgical device is provided that can include an access device. Further, the access device can include an inner sidewall, an outer sidewall, a proximal end, a distal end, and an opening extending between the proximal and distal ends to receive an instrument therethrough, and one or more structures can be coupled to the outer surface. Still further, the one or more structures can include a first surface and a second surface, such that the first surface contacts the tissue during advancement of the access device in an insertion direction into a body of a patient, and is configured to minimize friction between the first surface and tissue, and the second surface contacts the tissue during advancement of the access device in a direction opposite to the insertion direction to prevent proximal movement of the device out of the body, and is configured to increase friction between the second surface and tissue.

The devices and methods described herein can have a number of additional features and/or variations, all of which are within the scope of the present disclosure. In some embodiments, for example, the one or more structures can be coupled to the outer surface at a flexion point. Further, the one or more structures can be configured to flex about the flexion point with respect to the access device. Still further, flexion of the structures about the flexion point can alternate the structures between the first surface and the second surface for contacting tissue.

In certain embodiments, the structures can flex due to friction with surrounding tissue. For example, in some embodiments, the structures can flex from approximately 20 degrees relative to the outer surface of the access port to approximately 180 degrees relative to the outer surface of the access device. In some embodiments, the surgical device can be entirely comprised of the access device having the one or more structures formed thereon. Further, in certain embodiments, the one or more structures on the outer surface can be positioned unidirectionally relative to one another. Still further, in some embodiments, the one or more structures can be formed on a sleeve that is coupled to the device. And in some embodiments, the surface structures can include a layer of biased fibers on the outer surface of the access device.

In certain embodiments, the one or more structures can project radially outward from the outer surface to prevent proximal movement of the device out of the body. Further, in some embodiments, the one or more structures can be arranged to point in a direction that is opposite of the insertion direction. The one or more structures, in certain embodiments, can further include any of teeth, fish scales, fins, flaps, skins, bristles, braids, hooks, and threads. And in certain embodiments, the one or more structures can be made of any of rubber, polystyrene, nylon, yarn, mohair, plastic, polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyetheretherketones (PEEK), polyarylether ketones (PAEK), polymethacrylic acid esters, polyacrylic acid esters, aromatic polyesters, polyimides, or polyamides.

In some embodiments, the second surface can include one or more edges configured to penetrate tissue to become disposed therein. And in some embodiments, the access device cannot be housed in another device during insertion.

In another aspect, a surgical method is provided that can include inserting an access device into a body of a patient. Further, the access device can include an inner surface, an outer surface, a proximal end, a distal end, an opening extending between the proximal and distal ends to receive an instrument therethrough, and one or more structures formed on an outer surface thereof. The method can further include translating the access device through the body in a first direction, the one or more structures traveling relative to the body; and deploying one or more structures from the outer surface of the access device to couple the structures to the body to increase friction between the structures and the body.

As with the above-described aspect, a number of additional features and/or variations can be included, all of which are within the scope of the present disclosure. In some embodiments, for example, a surface of the structures can contact tissue in the body of the patient during translation of the access device in the insertion direction. In some embodiments, the structures cannot be housed in another device during insertion. Further, in certain embodiments, deploying the structures can further include flexing of the structures relative to the outer surface. Still further, in certain embodiments, flexing of the structures can occur about a flexion point formed on the access device.

In certain embodiments, the surface structures can deploy due to friction with tissue. In some embodiments, deploying the structures can further include rotating the access device relative to its longitudinal axis in a first direction to deploy the structures into the tissue to prevent movement of the device relative to the body and rotating the access device relative to its longitudinal axis in a second, opposite direction to retract the structures to allow movement of the device relative to the body. And, in certain embodiments, the method can further include decoupling the structures from the body and withdrawing the access device from the body of the patient, the access device translating in a second, opposite direction to the insertion direction, the structures contacting tissue in the body of the patient during translation of the access device in the second direction.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The following detailed description is provided with the accompanying drawings, in which.

DETAILED DESCRIPTION

Surface features for device retention are disclosed herein, e.g., for retaining an access port within a patient during a surgical procedure. The surface features can prevent ejection of the access port from a body of a patient. The surface features can be positioned along the access port and configured to glide along body tissues with minimal friction so as not to hinder travel of the access port in an insertion direction. After insertion of the access port, the surface features can engage with surrounding tissue to increase friction therebetween and to prevent ejection of the access port from the patient. Deployment of the surface features can occur due to friction with the surrounding tissue and/or via activation of the surface features to protrude from the access port. The surface features can include teeth, hooks, scales, fins, bristles, braids, and/or threads for engaging tissue. The surface features can be disengaged from the tissue to enable withdrawal of the access port without damaging the surrounding tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1:
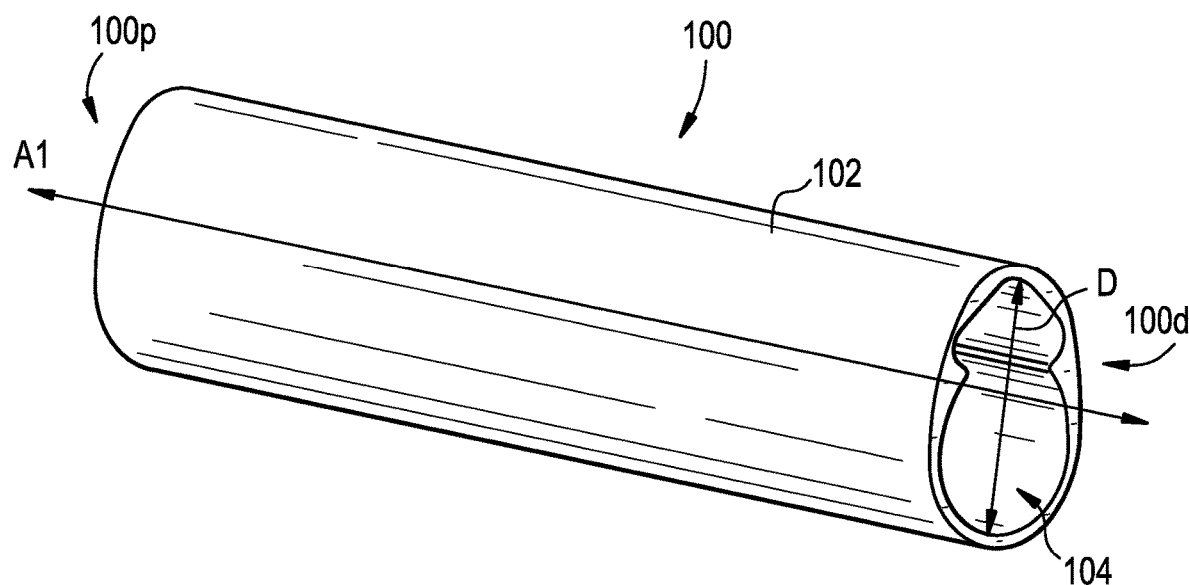
FIG. 1 is a perspective view of an exemplary access port.

FIG. 1 illustrates an exemplary embodiment of an access port 100 that can be inserted or slid into a patient. For example, the access port 100 can be used to create an access path for objects, e.g., devices such as bone anchors, instruments and/or surgical material, e.g., sutures, to be introduced into a surgical site. The access port 100 can include a generally tubular or cylindrical-shaped body defined by a sidewall 102 having a central opening 104. The opening 104 can extend along an axis A1 from a proximal end 100p of the access port 100 to a distal end of the access port 100d. In some embodiments, the opening 104 can be shaped to correspond with a shape of an object or an instrument being inserted therethrough. It will be appreciated that the access port 100 can be a cannula, tube, retractor, bladed retractor, dilator, and/or another example of an access device known to one having ordinary skill in the art for creating an access path into a surgical site of a patient. As shown, the access port 100 can have a uniform diameter D, though, in some embodiments, the access port 100 can have two or more diameters.

The access port 100 disclosed herein can be made from a rigid or a flexible material. Some non-limiting examples of rigid materials can include stainless steel, titanium, nickel, cobalt-chromium, or alloys and combinations thereof, polymers such as PEEK, ceramics, carbon fiber, and so forth. Some non-limiting examples of flexible materials can include rubber, any of a variety of flexible polymers, and so forth. The material can be chosen based on the surgical site, type of surgery, and/or the objects used during the procedure. Rigid materials can provide added support for objects introduced into the surgical site, while flexible materials can be more easily manipulated by a surgeon to increase an amount of space at the surgical site. It will be appreciated that flexible materials that are sufficiently deformable can allow the access port to be removed when intended, without damaging surrounding tissue. For example, in some embodiments an access port can be made from a flexible woven material that can allow the access port to dynamically change size based on whatever instrument, implant, etc. is being passed therethrough. Such a construction can minimize tissue damage by minimizing a size of the port passing through tissue during times when, e.g., no instrument (or a small instrument) is being passed therethrough. Such woven ports, however, can be particularly susceptible to backing out in response to muscle activity and, as a result, can benefit from inclusion of the surface features described herein.

The sidewall 102 of the illustrated access port 100 can be smooth to facilitate insertion of the access port with minimal friction. While minimizing damage to surrounding tissue, having a smooth sidewall 102 can make the access port 100 prone to unintended backing out of the patient. In some embodiments, surface structures can be added to the access port 100 to retain the access port within the surgical site and prevent ejection, as described further below.

Figure 2:
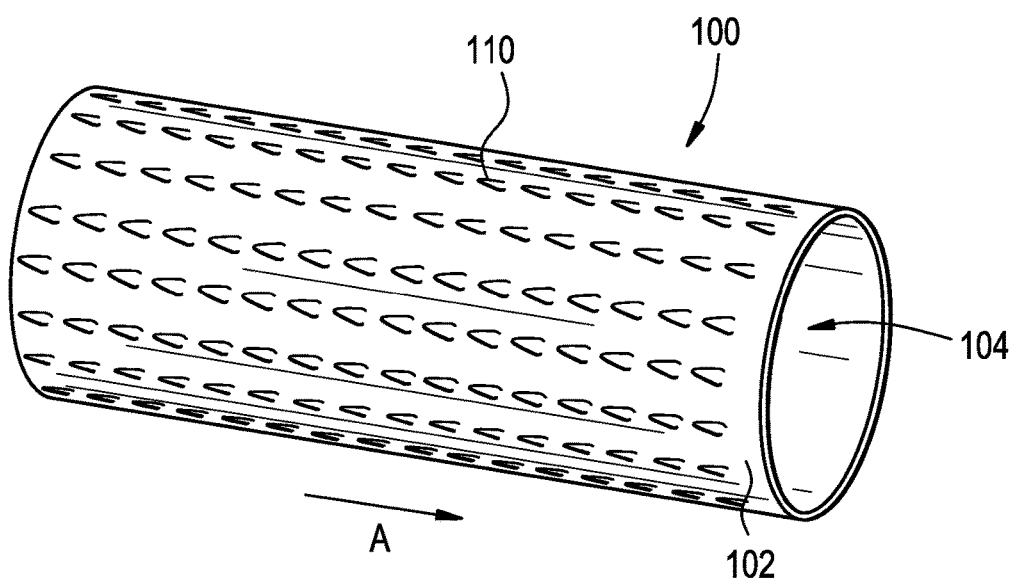
FIG. 2 is a perspective view of an access port having surface features thereon.

FIG. 2 illustrates an exemplary embodiment of an access port 100 having surface features 110 that can be used to retain and/or anchor the access port 100. For example, the surface features 110 can prevent axial ejection of the port 100 from the surgical site. The surface features 110 can be formed on, or attached to, the sidewall 102 of the access port 104. The surface features 110 can protrude from the sidewall 102 to modify and/or alter the sidewall 102.

In some embodiments, the surface features 110 can include a roughening of the sidewall 102 to modify the structure thereof. The surface features 110 can create a counter-friction when the sidewall 102 engages with tissue. More particularly, roughening the sidewall 102 increases friction between the sidewall 102 and the tissue to help minimize and/or prevent the risk of unintended ejection of the access port 102. The surface features 110 can be shaped such that any tearing of tissue is minimized during insertion and ejection of the access port 102. For example, the surface features 110 can have gliding properties in an insertion direction A so as to minimize friction in the insertion direction A and not hinder insertion, as described further below.

The surface features 110 can engage and/or become disposed in tissue at the surgical site to create counter-friction therebetween, thereby preventing ejection of the access port. The surface features 110 can be formed integrally with the access port 110, or can be separate components that are welded, threaded, glued, thermally or mechanically fixed, or otherwise associated with the access port. In some embodiments, the surface features 110 can be formed on a sleeve that can be coupled, threaded, glued, thermally or mechanically fixed, or otherwise associated with the access port, as further described below.

The surface features 110 can be arranged along the sidewall 102 extending from the proximal end 100p to the distal end 100d of the access port 100, as shown, though, in some embodiments, the surface features 110 can be located on one or more of the proximal portion 100p, the distal portion 100d, or an intermediate portion.

Varying a location of the surface features 110 on the access port 100 can affect a location at which the access port will be disposed. In some embodiments, a distal-most end of the access port 100, e.g., approximately 1-10 mm of the distal-most end, approximately 3-7 mm of the distal-most end, or approximately 5 mm of the distal-most end, can be free of surface structures. Allowing a sidewall 102 free of surface features to be introduced into the surgical site prior to the access port 100 have surface features 110 thereon can gradually dilate the surgical site to prepare the patient for introduction of the surface features therein.

In use, the access port 100 can be advanced distally in an insertion direction A into the surgical site. During insertion of the access port 100, the surface features 110 can travel along a surface of the tissues without becoming engaged therein. It will be appreciated that the surface features 110 can be oriented to minimize friction with the tissue when the access port is being advanced to allow the access port to be advanced to the desired location. Once inserted, the surface features 110 can engage surrounding tissue to prevent ejection of the access port 100. In some embodiments, the surface features 110 can deploy due to friction with the surrounding tissue, or can actively deploy to engage surrounding tissue, as described further below. After engaging tissue to be sufficiently secured at the desired location, devices, instruments, and other materials can be introduced into the body of the patient through the access port 100. At the conclusion of the surgical procedure, the surface features 110 can disengage from the tissues and the access port 100 can advanced in a direction opposite to the insertion direction A, e.g. proximally, to remove the access port 100 from the surgical site. It will be appreciated that the surface features 110 can be sufficiently manipulated to disengage from the tissue to allow the port to be removed from the surgical site when intended without damaging surrounding tissues.

FIGS. 3-10 illustrate a number of variations on the surface features described above. Except as indicated or as will be readily appreciated by one having ordinary skill in the art having read the present disclosure, the structure and operation of these variations is substantially the same as that of the surface features described above and therefore a detailed description is omitted here for the sake of brevity.

Figure 3:
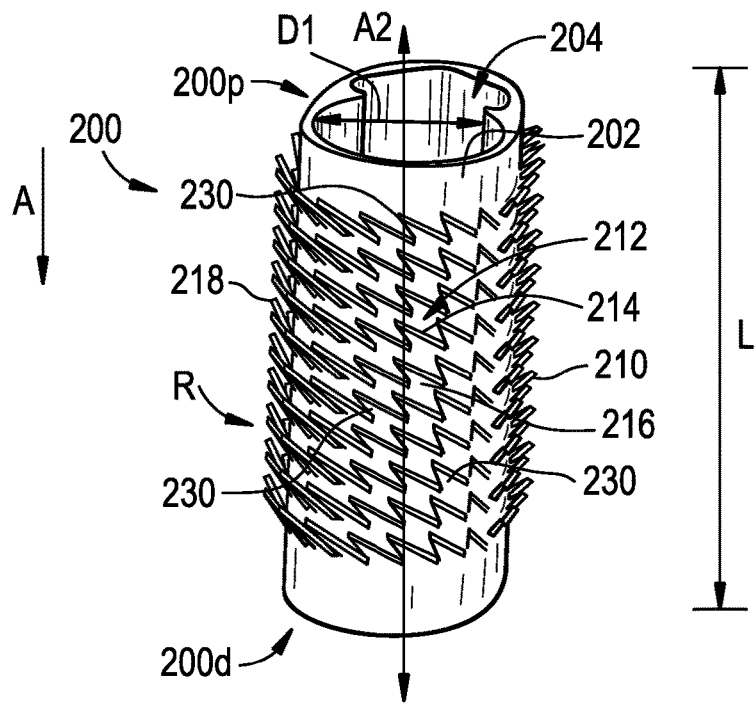
FIG. 3 is a perspective view of a sleeve that can be used with the access port of FIG. 1.

FIG. 3 illustrates an exemplary embodiment of a sleeve 200 having surface features or teeth 210 attached thereto. The sleeve can include a generally tubular or cylindrical-shaped body defined by a sidewall 202 having a central opening 204. The opening 204 can extend along an axis A2 from a proximal end 200p of the sleeve to a distal end 200d of the sleeve 200, which can be parallel to the axis A1 that extends through the access port 100. In some embodiments, the opening 204 can be shaped to correspond with a shape of an object or an instrument being inserted therethrough. As shown, the sleeve can have a uniform diameter D1, though, in some embodiments, the sleeve 200 can have two or more diameters. In some embodiments, the diameter D1 of the sleeve 200 can be equal to the diameter D of the access port 100, though, in some embodiments, the diameter D1 of the sleeve 200 can be larger and/or smaller than the diameter D of the access port 100.

One or more surface features 210 can extend from the sidewall 202 of the sleeve 210. As shown, the surface features 210 can resemble teeth that penetrate tissue to secure the access port thereto. The teeth can have one or more edges 212 for grasping surrounding tissue. As shown, the teeth can have a leading edge 214 and a trailing edge 216. The leading edge 214 can have a sharp surface that penetrates the tissue to retain the access port 100 at a given location. The trailing edge 216 can follow the leading edge 214 into the tissue to provide an additional point of engagement for the teeth with the tissue.

While teeth having two edges are shown, it will be appreciated that, in some embodiments, teeth having one edge, or three or more edges can be used. Similarly, while the surface features have a generally triangular shape, as shown, the surface features 210 can be rectangular, square, pentagonal, hexagonal, and so forth. Surface features of different shapes can include a smaller or larger number of edges 214 that can engage tissue. The greater the number of edges 212 of each surface feature 210 that can engage with tissue, the more stable the retention of the access port 100 in the surgical site, which can reduce the chances that the access port 100 can be ejected unintentionally from the surgical site.

As shown, the surface features 210 can be arranged uniformly along a circumference of the sleeve 200, though it will be appreciated that alternate arrangements with random and/or non-uniform distribution of surface features 210 are possible. The size, number, and spacing of the surface features 210 can be selected based on the type of surgical procedure, the location of the surgical site, and a degree of securement desired to prevent ejection of the access port.

For example, as shown, the surface features 210 can be arranged in one or more rings R along a circumference of the sleeve 200. Arranging the surface features in rings can allow the surface features 210 to be distributed throughout the circumference of the sleeve 200, which can allow the sleeve to be inserted into the surgical site in any orientation. Each surface feature 210 can be equally spaced from each adjacent surface feature, as shown, though, in some embodiments, equal spacing between adjacent surface features is not maintained. Equal spacing between surface features 210 can allow for maximum flexion of each surface feature 210 during insertion and ejection without interference from adjacent surface features, as described further below.

The number of surface features 210 per ring R can vary based on a diameter D1 of the sleeve 200. Each ring R can include approximately five surface features thereon, approximately ten surface features thereon, approximately fifteen surface features thereon, and/or approximately twenty or more surface features thereon. Likewise, the number of rings formed on the sleeve 200 can vary based on a length L of the sleeve 200. Each sleeve can include approximately two rings thereon, approximately five rings thereon, approximately ten rings thereon, and/or approximately fifteen or more rings thereon. It will be appreciated that a larger number of surface features 210 formed on the sleeve can increase a strength of the engagement between the surface features 210 and the tissue.

The surface features 210 can be manufactured such that no other component or device houses the surface features 210 during insertion. The surface features 210 can include gliding properties thereon so as not to hinder advancement of the access port through the surgical site. For example, the surface features 210 can include a top surface 230 that glides along a surface of the tissue during advancement of the access port in the insertion direction A. The top surface 230 can be manufactured from materials having a low coefficient of friction to facilitate insertion while preventing inadvertent engagement and/or damage to tissue during insertion. In some embodiments, the surface features 210 can be withdrawn into an interior of the access port 100 so as to prevent contact of the tissue during insertion of the access port.

The surface features 210 can flex and/or pivot relative the sidewall 202. Flexing of the surface features 210 can reduce and/or minimize friction with surrounding tissue. As shown, the surface features 210 can protrude from the sidewall 202 at an angle with respect to the sidewall 202. The angle of the surface feature 210 can be such that a force applied by tissues during insertion of the sleeve 200 in the insertion direction A can flex the surface features 210 towards the sidewall to decrease the angle of the surface feature 210 relative to the sidewall 202. The degree to which the surface features 210 can flex with respect to the sidewall 202 is discussed in further detailed with regards to the embodiments below, while still applying to the instant embodiment.

The surface features can be formed and/or manufactured from a soft, elastic and/or a flexible material, e.g., rubber, polystyrene, nylon, yarn, mohair, plastic, that can bend and/or flex. In some embodiments, the surface features 210 can be formed from a material of the sleeve, e.g., by cutting a series of flaps into the sleeve and/or the access port, molded, extruded, or any other technique known in the art for manufacturing surface features. In some embodiments, one or more of fish scales, fins, flaps, skins, hairs, hooks, threads, and/or other examples of features known to one skilled in the art for engaging tissue can be used in lieu of, or in addition to, teeth to increase friction with surrounding tissue.

The surface features 210 can deploy from the access port 100 in a variety of ways. For example, the surface features 210 can be arranged to point in a given direction such that motion in an opposite direction activates the surface features 210, causing them to flex and engage surrounding tissues. As shown in FIG. 3, the surface features 210 can be arranged to point proximally, e.g., in a direction substantially opposite of the insertion direction A of the sleeve 200. A tip 218 of the surface features can point at an angle that is approximately 155 degrees with respect to the insertion direction A, approximately 165 degrees with respect to the insertion direction A, approximately 175 degrees with respect to the insertion direction A, and/or approximately 180 degrees with respect to the insertion direction A.

When the tip 218 points substantially opposite to the insertion direction A, during advancement in the insertion direction, the surrounding tissue imparts a force onto the surface features 210 that causes them to flex to lie against the sidewall 102. In this position, in some embodiments, the edges 212 of the surface features 210 do not engage the surrounding tissue. Rather, the surface features 210 are flexed such that the top surface contacts tissue to slide therealong. Once advancement is stopped, the force on the surface features 210 decreases, causing them to return to their initial position. During removal of the access port 100, friction between the surface features and the tissue can cause the surface features 210 to deploy to flex in a direction that is perpendicular to the insertion direction A to engage the tissue, which resists removal of the access port 100. In some embodiments, the surface features 210 can actively deploy by virtue of being made from a shape memory material and/or via mechanical actuation such as a deployment sleeve or another deployment means known to one skilled in the art.

Figure 4A:
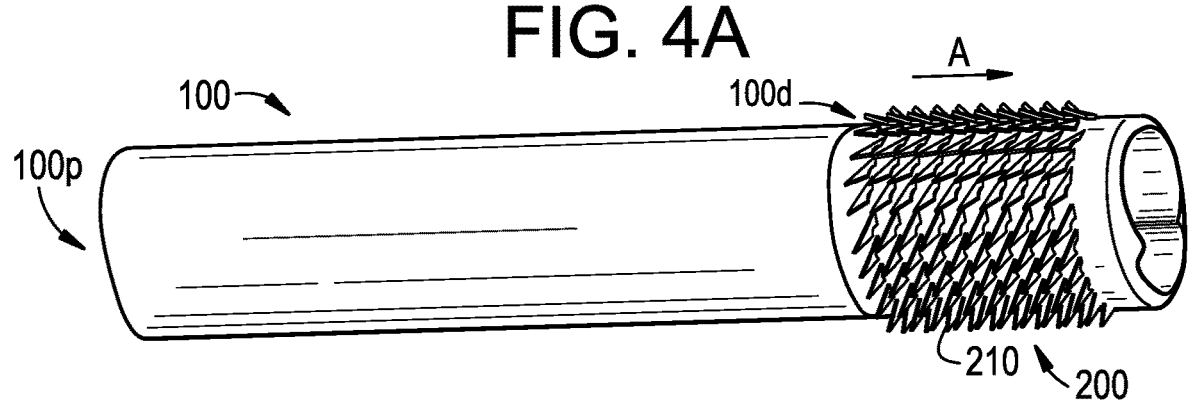
FIG. 4A is a perspective view of the sleeve of FIG. 3 coupled to the access port of FIG. 1.
Figure 4B:
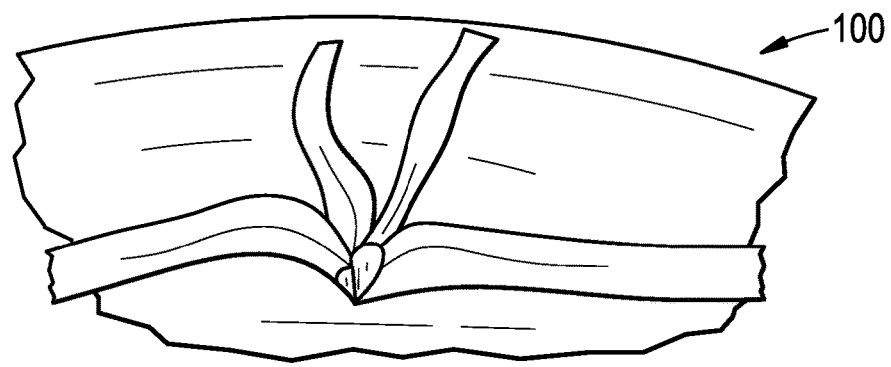
FIG. 4B is a perspective view of the access port of FIG. 4A cut open while inserted into a patient.

The sleeve 200 can be coupled to a distal end 100d of the access port 100, as shown in FIG. 4A, though, in some embodiments the sleeve 200 can be coupled to the proximal end 100p of the access port 100, be formed integrally with the port 100, conform to an outer shape of the access port 100, or slide over the access port 100 to receive the access port therein. The access port 100 can be manufactured from the same material as the sleeve 200, though, in some embodiments, the access port 100 can be flexible while the sleeve 200 is more rigid. Use of a flexible access port 100 can allow for a greater degree of manipulation of the access port 100 during the procedure to provide a surgeon with more room to operate. In some embodiments, after being inserted into the patient, the access port 100 can be cut such that the access port lies flush with the skin, as shown in FIG. 4B. Cutting the access port in this manner can increase access to the surgical site when performing surgery.

Figure 5:
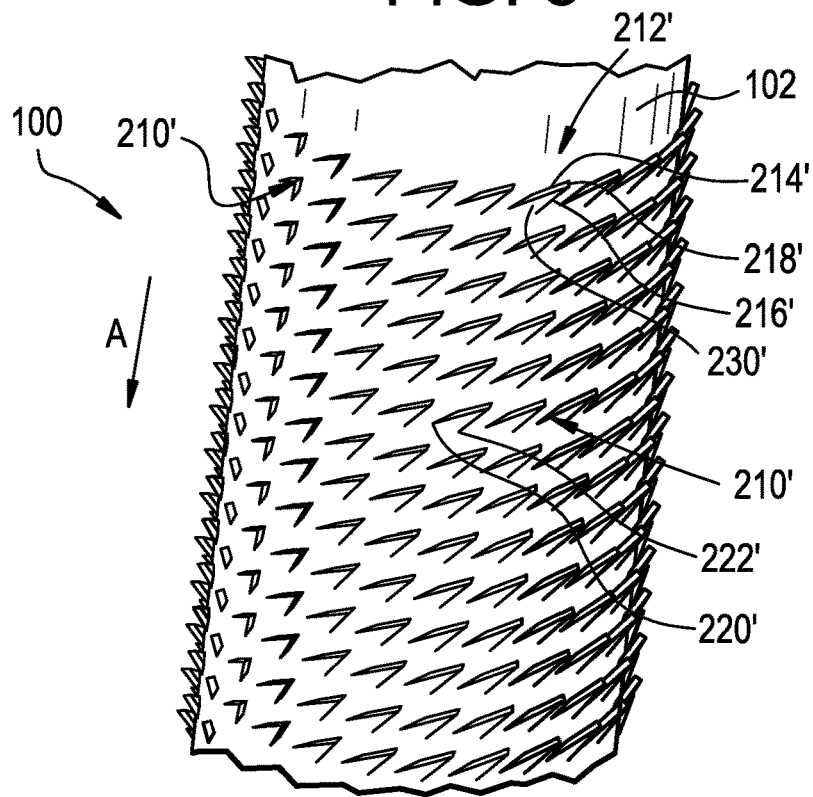
FIG. 5 is a perspective view of an exemplary embodiment of surface features formed on the access port of FIG. 1.

FIG. 5 illustrates an alternate embodiment of surface features 210' that can be used with the access port 100 described above. As shown, the surface features 210' can be coupled and/or attached directly to the sidewall 102 of the access port 100. As discussed with regards to the embodiments above, a leading edge 214' and a trailing edge 216' of the surface features 210' can come to a pointed tip 218' at one of the edges 212' of the surface features 210' to penetrate tissue.

Flexion of the surface features 210' can vary based on a shape and orientation of the surface features 210' on the sidewall 202. For example, the surface features 210' can have one or more flexion points along the access port 100. Flexion points can determine a degree of flexion of a surface feature 210' with respect to the access port 100 and/or the direction in which each surface feature 210' can flex and/or pivot. As shown in FIG. 5, each surface feature 210' includes two flexion points 220', 222' at a location where the surface feature 210' meets the access port 100, the flexion points resembling a base of an oblique triangle. As mentioned above, while the surface features have a generally triangular shape, as shown, the surface features 210 can be rectangular, square, pentagonal, hexagonal, and so forth. The surface features 210' can include one, or three or more flexion points that connect the surface features 210' to the access port to allow flexion relative therewith.

The number of flexion points can determine a direction and/or plane about which the surface feature can pivot. For example, as shown in FIG. 5, the surface features 210' can pivot about flexion points 220', 222'. The surface features 210' can pivot about both flexion points from being substantially parallel to an insertion direction A of the access port 100 to being substantially perpendicular to the insertion direction A. Pivoting of the surface features 210' about both flexion points 220', 222' can occur during insertion and/or withdrawal of the access port 100 from the surgical site and during engagement and disengagement with surrounding tissue.

A distance between flexion points can also determine the degree of flexion of a surface feature relative to the sidewall 202. For example, increasing a distance between flexion points can increase stiffness of the surface features, thereby limiting the degree to which surface features can flex and/or bend. The surface features 210' can flex about flexion points 220', 222' approximately to 10 degrees relative to the sidewall of the access port, can flex approximately to 25 degrees relative to the sidewall of the access port, can flex approximately to 45 degrees relative to the sidewall of the access port, can flex approximately to 65 degrees relative to the sidewall of the access port, can flex approximately to 75 degrees relative to the sidewall of the access port, and/or can flex approximately to 90 degrees relative to the sidewall of the access port.

Figure 6:
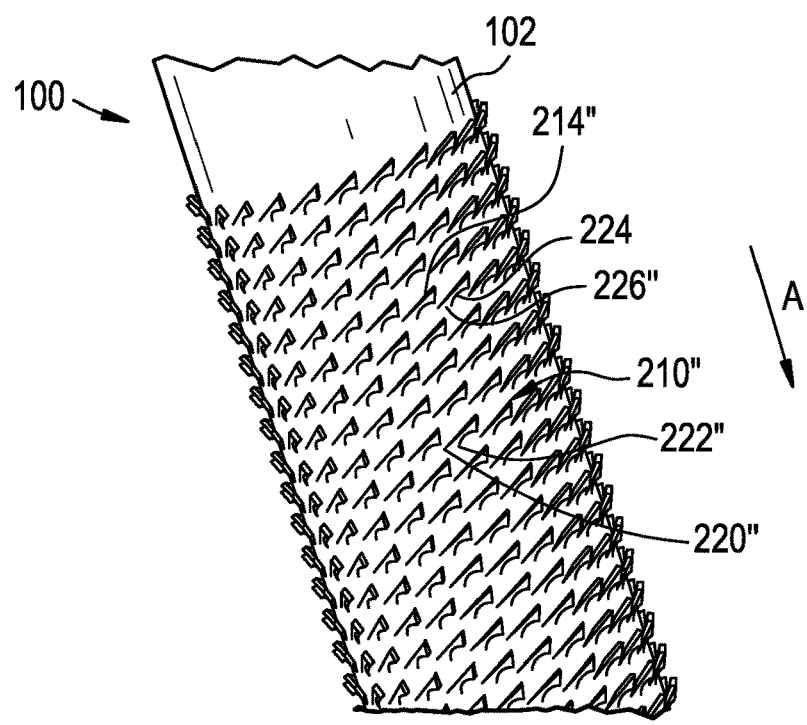
FIG. 6 is a perspective view of another exemplary embodiment of surface features formed on the access port of FIG. 1.

FIG. 6 illustrates an alternate embodiment of surface features that can be used with the access port described above. The surface features 210" can include a hooking feature 224 thereon to increase counter-friction and retention within the tissue to prevent backing out. As shown, the hooking feature 224 can be formed in a trailing edge 216", though it will be appreciated that, in some embodiments, the hooking feature 224 can be formed in a leading edge 214".

The surface features 210" can have one or more additional features for increasing the flexibility and/or decreasing the stiffness of the surface features. For example, as shown, the trailing edge 216" can include a hinge 226 formed therein. The hinge 226 can be cut-out from the surface feature 210" or formed as a notch in the surface feature. The hinge 226 decreases the stiffness of the surface feature 210", thereby allowing the surface feature to move across a larger degree of flexion.

The surface features 210" can include two flexion points 220", 222". As discussed above, when a distance between flexion points is reduced, the degree of flexion of a surface feature relative to the sidewall 202 increases. For example, the surface features 210" can flex about flexion points 220", 222" approximately to 20 degrees relative to the sidewall of the access port, can flex approximately to 50 degrees relative to the sidewall of the access port, can flex approximately to 70 degrees relative to the sidewall of the access port, can flex approximately to 90 degrees relative to the sidewall of the access port, can flex approximately to 120 degrees relative to the sidewall of the access port, and/or can flex approximately to 145 degrees relative to the sidewall of the access port, which represents a larger degree of flexion than the embodiment of FIG. 5.

Figure 7:
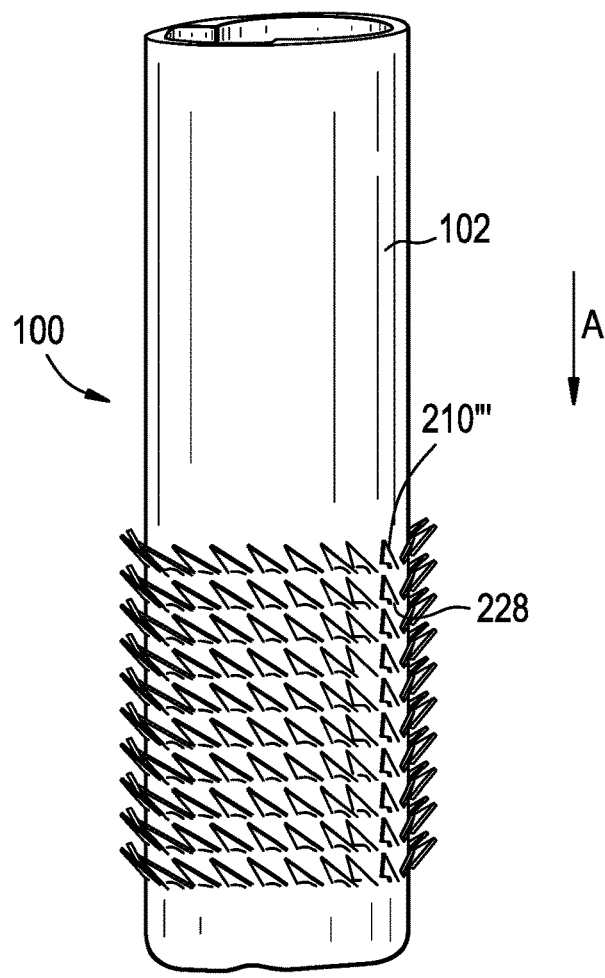
FIG. 7 is a perspective view of another exemplary embodiment of surface features formed on the access port of FIG. 1.

FIG. 7 illustrates an alternate embodiment of surface features that can be used with the access port described above. The surface features 210''' can be attached to the access port 100 via a flange 228. As shown, the surface features 210''' can pivot, bend, and/or flex relative to the access port about the flange 228 during insertion, retention, and/or withdrawal. The narrow distance between the contact points 220''', 222''' of the flange can allow the surface feature 210''' to flex approximately to 30 degrees relative to the sidewall of the access port, to flex approximately to 70 degrees relative to the sidewall of the access port, to flex approximately to 90 degrees relative to the sidewall of the access port, to flex approximately to 120 degrees relative to the sidewall of the access port, to flex approximately to 145 degrees relative to the sidewall of the access port, to flex approximately to 165 degrees relative to the sidewall of the access port, and/or to flex approximately to 180 degrees relative to the sidewall of the access port which represents a larger degree of flexion than the embodiments of FIGS. 5 and 6.

The durability and/or stiffness of the material used to form the surface features can also impact flexion. The surface features 210', 210", 210''', as discussed with regards to FIGS. 5-7, as well as the remainder of the embodiments discussed herein, can be formed and/or manufactured from a soft, elastic and/or a flexible material, e.g., rubber, polystyrene, nylon, yarn, mohair, plastic, that can bend and/or flex. In some embodiments, the surface features 210', 210", 210''' can be formed from a material of the sleeve, e.g., by cutting a series of flaps into the sleeve and/or the access port, molded, extruded, or any other technique known in the art for manufacturing surface features. In some embodiments, one or more of fish scales, fins, flaps, skins, hairs, hooks, threads, and/or other examples of features known to one skilled in the art for engaging tissue can be used in lieu of, or in addition to, the surface features described herein to increase friction with surrounding tissue.

Figure 8:
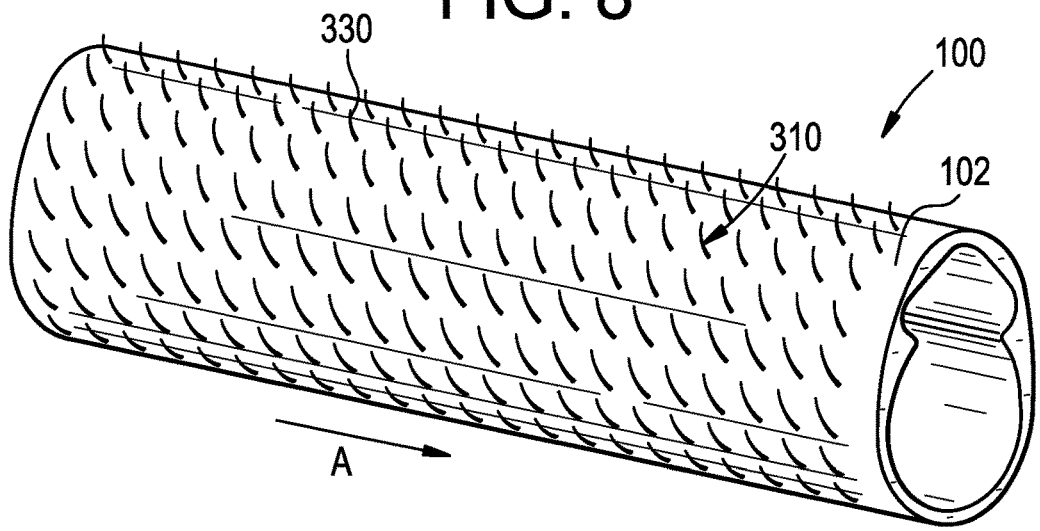
FIG. 8 is a perspective view of another exemplary embodiment of surface features on the access port of FIG. 1.

FIG. 8 illustrates an alternate embodiment of surface features 310 that can be used with the access port 100 described above. As shown, the surface features can include a layer of biased structures 310 formed and/or attached to the sidewall 102 of the access port 100. The structures 310 can be attached by strips or sleeves onto the sidewall 102. In some embodiments, the structures 310 can be formed on a sleeve (not shown) that can be pulled over the access port 100.

Similar to the embodiments described above, the biased structures 310 can be arranged such they point unidirectionally. The biased structures 310 can then flex in a given direction to facilitate insertion of the access port 100 in the insertion direction A. In some embodiments, the structures can flex from approximately 0 degrees to approximately 180 degrees relative to the sidewall 102 of the access port. The structures 310 can include top surfaces 330 for engaging tissue. During advancement in the insertion direction A, the tissue can exert a force on the structures 310 to flex the structures such that the top surfaces 330 point away from the tissue to minimize friction during advancement. Movement in the opposite direction can bring the top surfaces 330 in contact with the tissue, causing the structures to adhere to tissues and create counter-friction to prevent backing out.

The structures can be formed and/or manufactured from a soft, elastic and/or a flexible material, e.g., rubber, polystyrene, nylon, yarn, mohair, plastic, that can bend and/or flex. In some embodiments, the surface features 310 can be formed from a material of the sleeve, e.g., by cutting a series of flaps into the sleeve and/or access port, molded, extruded, or any other technique known in the art for manufacturing surface features. In some embodiments, one or more of fish scales, fins, flaps, skins, teeth, hooks, threads, and/or other examples of features known to one skilled in the art for grasping tissue can be used in lieu of, or in addition to, the structures described herein to increase friction with surrounding tissue.

Figure 9A:
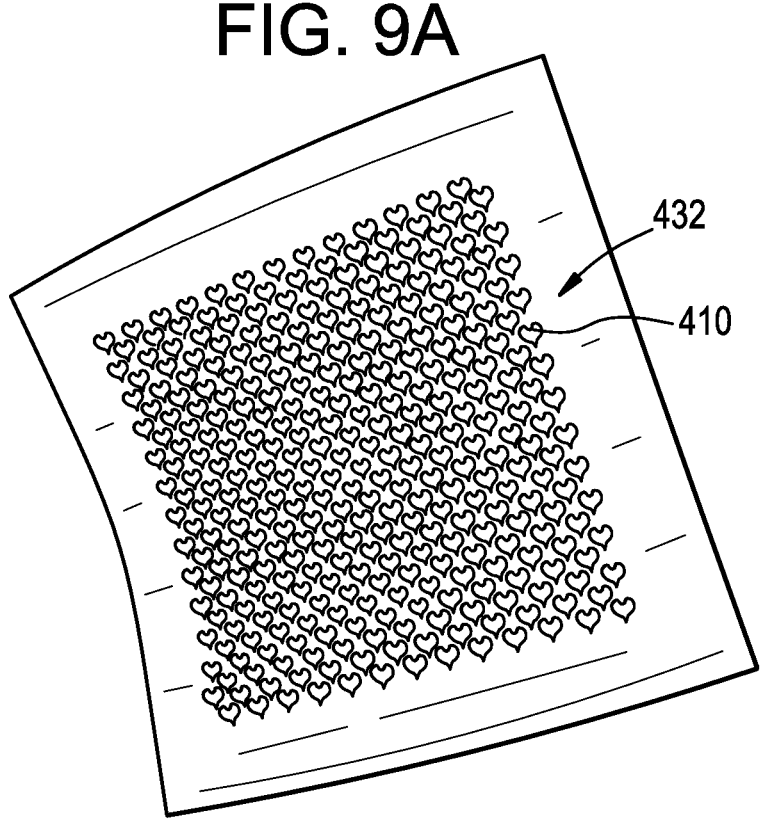
FIG. 9A is perspective view of another exemplary embodiment of surface features on a sheet material.
Figure 9B:
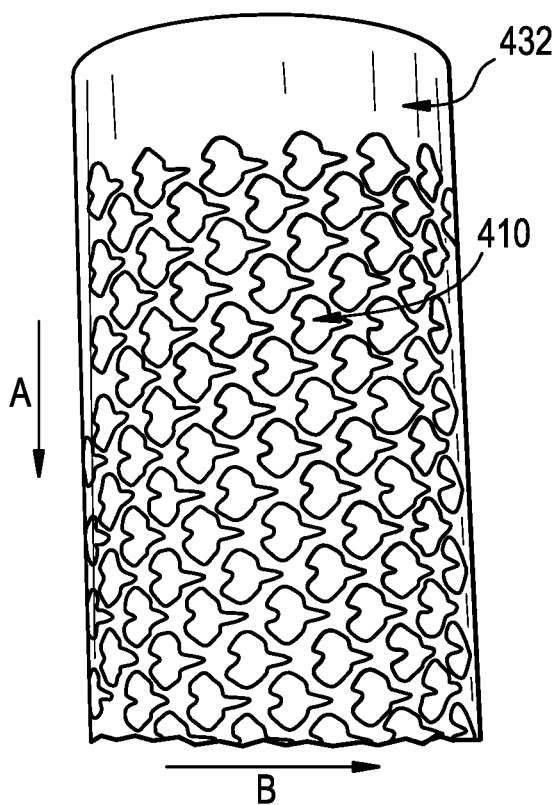
FIG. 9B is a detail perspective view of the surface features of FIG. 9A.
Figure 9C:
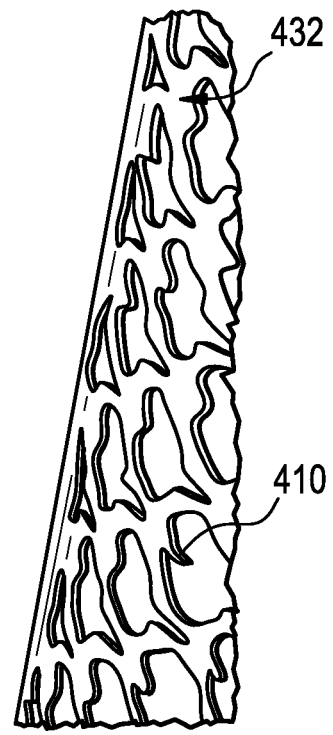
FIG. 9C is a side perspective view of the surface features of FIG. 9A.

FIGS. 9A-9C illustrate another exemplary embodiment of surface features or hooks that can be used with the access port described above. As shown, the hooks 410 can be printed on a sheet and/or film 432 for being attached to the sidewall 102 of the access port 100. The film 432 can have one or more surface features 410 that project radially outward from a surface thereof to engage with tissue. The film 432 can be fabricated using laser cutting machines and/or any other technique known to one skilled in the art, e.g., extrusion punched and/or laser cut having specifically defined shapes therein. As shown in FIG. 9B, the surface features are shaped like hooks, though it will be appreciated that the features can include one or more of fish scales, fins, flaps, skins, hairs, teeth, threads, and/or other examples of features known to one skilled in the art for grasping tissue can be used in lieu of, or in addition to, the hooks described herein to increase friction with surrounding tissue. In some embodiments, the surface features can be formed and/or manufactured from a soft, elastic and/or a flexible material that can bend and/or flex, e.g., rubber, polystyrene, nylon, yarn, mohair, plastic, polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyetheretherketones (PEEK), polyarylether ketones (PAEK), polymethacrylic acid esters, polyacrylic acid esters, aromatic polyesters, polyimides, and/or polyamides. In some embodiments, the surface features 410 can be formed from a material of the sleeve, e.g., by cutting a series of flaps into the sleeve and/or access port, molded, extruded, or any other technique known in the art for manufacturing surface features.

The hooks 410 can point unidirectionally to reduce and/or minimize friction during advancement of the sleeve 200 and/or the access port 100 in the insertion direction A. For example, as shown in FIGS. 9B-9C, the hooks 410 can extend in a direction B that is substantially perpendicular to the insertion direction A of the access port 100 to engage tissue, though, in some embodiments, the hooks 410 can point proximally, e.g., in a direction opposite to the insertion direction A, as discussed above, or at an oblique angle with respect to the insertion direction A. Engaging tissue in a direction perpendicular to the insertion direction A can enhance retention of the access port 100 by increasing the counter-friction with the surrounding tissue. Once the hooks 410 have engaged tissue, exertion of a proximal force onto the access port is less likely to disengage the hooks 410 from the tissue, which will prevent unwanted ejection of the access port.

The film 432 can be wrapped around the sidewall 102 and mechanically fixed thereto, though, in some embodiments, the film 432 can be welded, threaded, glued, thermally or mechanically fixed, or otherwise associated with the access port to engage with tissue. In some embodiments, the film 432 can be manufactured to form a helically-shaped hook pattern, though it will be appreciated that a variety of patterns can be imprinted on the film.

Figure 10A:
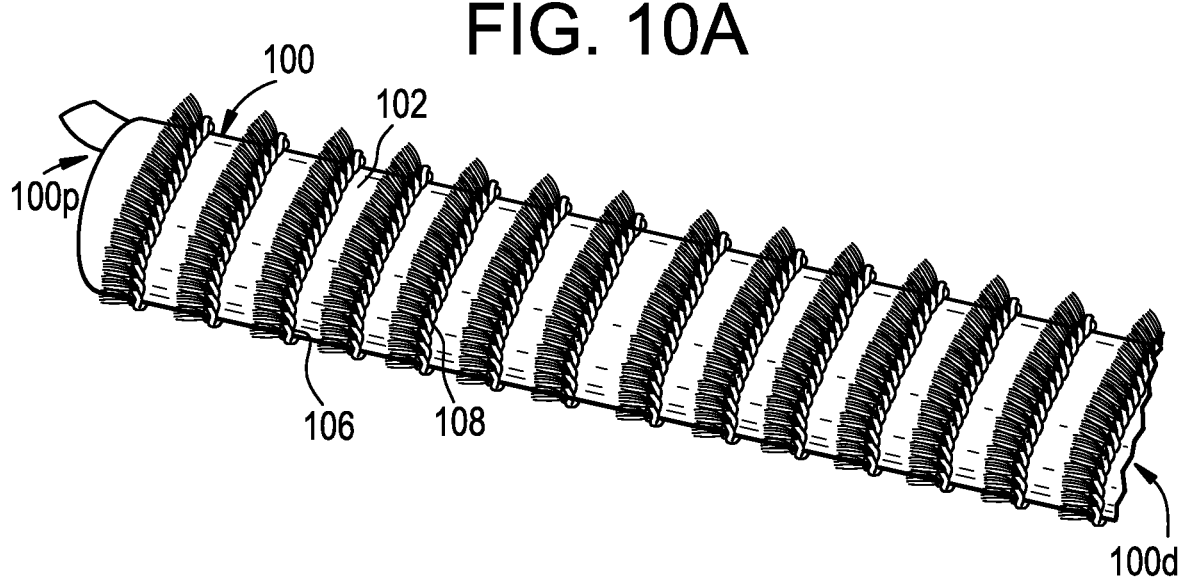
FIG. 10A is another exemplary embodiment of surface features formed on the access port of FIG. 1.
Figure 10B:
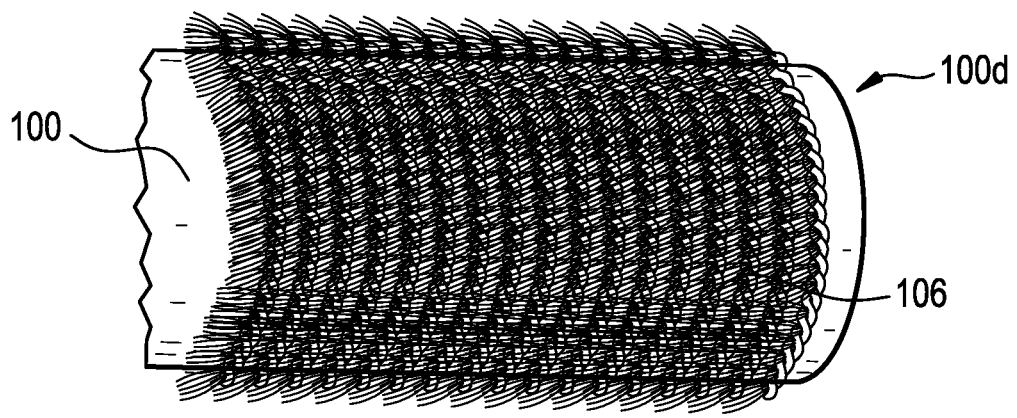
FIG. 10B is a detail perspective view of the surface features of FIG. 10A.
Figure 10C:
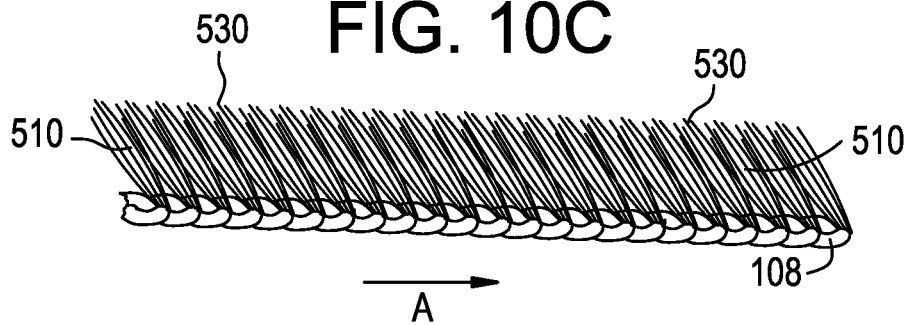
FIG. 10C is a detail perspective view of the surface features of FIG. 10A, showing a main strand having bristles thereon.

FIGS. 10A-10C illustrate another exemplary embodiment of surface features that can be used with the access port described above. As shown in FIG. 10A, the access port 100 can include a groove 106 in the sidewall 102 thereof. The groove 106 can be formed in a helical shape, as shown. The groove 106 can extend from the proximal end 100*p* to the distal end 100*d* of the access port 100, as shown, or it can extend through a single end of the port, as shown in FIG. 10B.

The groove 106 can include a main strand 108 therein. The main strand 108 can be seated in the groove 106 such that the main strand 108 does not protrude from the groove 106, though, in some embodiments, the main strand 108 can extend from the groove 106 or wrap around the sidewall 102 between adjacent portions of the groove. The main strand 106 can include a single, continuous piece of filament or yarn that extends through the groove, or the main strand 108 can be composed of two or more strands that are glued, tied, wrapped, thermally or mechanically fixed, or otherwise associated with one another and/or the groove. The main strand 108 can extend through an entire length of the groove 106, as shown in FIG. 10B, in which the groove is located on a distal end of the access port, or through a portion of the groove. In some embodiments, the main strand 108 can be fixed to the groove 106 at its first end and at its second end, though, in some embodiments, the main strand 108 can be fixed to the groove 106 at more than two points or throughout its length.

The main strand 108 can include one or more surface features or bristles 510 that protrude therefrom. The bristles 510 can be hair-like projections that extend from the main strand 108. As shown in FIG. 10C, the bristles 510 can extend can point substantially unidirectionally from the main strand 108 to reduce and/or minimize friction during advancement of the sleeve 200 and/or the access port 100 in the insertion direction A, though, in some embodiments, the bristles 510 can extend in multiple directions to engage tissue. The bristles 510 can be formed and/or manufactured from a soft, elastic and/or a flexible material that can bend and/or flex, e.g., rubber, polystyrene, nylon, yarn, mohair, plastic, polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyetheretherketones (PEEK), polyarylether ketones (PAEK), polymethacrylic acid esters, polyacrylic acid esters, aromatic polyesters, polyimides, and/or polyamides. In some embodiments, the bristles 510 can be formed from a material of the sleeve, e.g., by cutting a series of flaps into the sleeve and/or access port, molded, extruded, or any other technique known in the art for manufacturing surface features. In some embodiments, one or more of fish scales, fins, flaps, skins, teeth, hooks, threads, and/or other examples of features known to one skilled in the art for grasping tissue can be used in lieu of, or in addition to, the structures described herein to increase friction with surrounding tissue.

During insertion of the access port 100 of the instant embodiment into the surgical site, the bristles can flex outward to protrude from the sidewall to engage surrounding tissue to retain the port at the desired location. In some embodiments, the bristles 510 can flex from approximately 0 degrees to approximately 180 degrees relative to the sidewall 102 of the access port. The bristles 510 can include top surfaces 530 for engaging tissue. During advancement in the insertion direction A, the tissue can exert a force on the bristles 510 to flex the bristles such that the top surfaces 530 point away from the tissue to minimize friction during advancement. Movement of the access port in the opposite direction can bring the top surfaces 530 in contact with the tissue, causing the structures to adhere to tissues and create counter-friction to prevent backing out.

In use, an incision can be made in the surgical site of the patient. The access port 100 having one or more of the surface features discussed in the embodiments above can be positioned near the surgical site and advanced distally therethrough in an insertion direction A. The access port 100 can be inserted and advanced through the surgical site by pushing, via rotation, or by any other method known to one in the art for inserting instruments into a surgical site to minimize damage to surrounding tissue. During insertion and advancement, the surface features can bend, flex, and/or pivot toward the sidewall of the access port and/or away from the tissue so as to create minimal friction between the surface features and surrounding tissues to allow advancement of the access port.

Once advanced to the desired location, the surface features can be deployed to engage surrounding tissue to prevent ejection of the access port. The surface features can be deployed due to friction with surrounding tissue or actively deployed, e.g., by rotation the access port 100. For example, rotation of the access port 100 relative to its longitudinal axis A1 in a first direction can deploy the surface features to engage the tissue to prevent movement of the device relative to the tissue and rotation of the access port relative to its longitudinal axis A1 in a second, opposite direction can disengage the surface features from the tissue to allow retraction of the access port 100 from the surgical site. Devices, instruments, and other materials can then be introduced into the body of the patient through the access port. At the conclusion of the procedure, the surface features can be withdrawn from the tissues and the access port 100 can advanced in a direction opposite to the insertion direction A, e.g. proximally, to remove the access port 100 from the patient. It will be appreciated that the surface features can be sufficiently manipulated to allow the port to be removed from the surgical site when intended without damaging surrounding tissues.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of navigated surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A surgical device, comprising:
    an access device having an inner sidewall, an outer sidewall, a proximal end, a distal end, and an opening extending between the proximal and distal ends to receive an instrument therethrough;
    one or more structures coupled to the outer surface, the one or more structures having a first surface and a second surface;
    wherein the first surface is configured to contacts a tissue during advancement of the access device in an insertion direction into a body of a patient, the first surface being configured to minimize friction between the first surface and the tissue,
    wherein the second surface is configured to contacts the tissue during advancement of the access device in a direction opposite to the insertion direction to prevent proximal movement of the device out of the body, the second surface being configured to increase friction between the second surface and the tissue, and
    wherein the one or more structures are configured to deploy due to friction with tissue.

2. The device of claim 1, wherein the one or more structures are coupled to the outer surface at a flexion point.

3. The device of claim 2, wherein the one or more structures are configured to flex about the flexion point with respect to the access device.

4. The device of claim 3, wherein flexion of the one or more structures about the flexion point alternates the one or more structures between the first surface and the second surface for contacting the tissue.

5. The device of claim 4, wherein the structures flex from approximately 20 degrees relative to the outer surface of the access port to approximately 180 degrees relative to the outer surface of the access device.

6. The device of claim 1, wherein the one or more structures are configured to flex due to friction with surrounding tissue.

7. The device of claim 1, wherein the surgical device is entirely comprised of the access device having the one or more structures formed thereon.

8. The device of claim 1, wherein the one or more structures on the outer surface are positioned unidirectionally relative to one another.

9. The device of claim 1, wherein the access device is not housed in another device during insertion.

10. The device of claim 1, wherein the one or more structures are formed on a sleeve that is coupled to the device.

11. The device of claim 1, wherein the one or more structures project radially outward from the outer surface to prevent proximal movement of the device out of the body.

12. The device of claim 11, wherein the one or more structures are arranged to point in a direction that is opposite of the insertion direction.

13. The device of claim 1, wherein the one or more structures further comprise any of teeth, fish scales, fins, flaps, skins, bristles, braids, hooks, and threads.

14. The device of claim 1, wherein the one or more structures are made of any of rubber, polystyrene, nylon, yarn, mohair, plastic, polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyetheretherketones (PEEK), polyarylether ketones (PAEK), polymethacrylic acid esters, polyacrylic acid esters, aromatic polyesters, polyimides, or polyamides.

15. The device of claim 1, wherein the second surface comprises one or more edges configured to penetrate tissue to become disposed therein.

16. The device of claim 1, wherein the one or more structures comprise a layer of biased fibers on the outer surface of the access device.

17. The device of claim 1, wherein the outer surface on which the one or more structures are formed is an outermost surface of the access device.

18. The device of claim 1, wherein the one or more structures are coupled to the outer surface around an entire circumference of the outer surface.

19. A surgical method, comprising:
inserting an access device into a body of a patient, the access device having an inner surface, an outer surface, a proximal end, a distal end, and an opening extending between the proximal and distal ends to receive an instrument therethrough, the access device having one or more structures formed on an outer surface thereof;
translating the access device through the body in a first direction, the one or more structures traveling relative to the body; and
deploying the one or more structures from the outer surface of the access device to couple the one or more structures to the body to increase friction between the one or more structures and the body, the one or more structures deploying due to friction with tissue.

20. The method of claim 19, wherein a surface of the one or more structures contacts tissue in the body of the patient during translation of the access device in the first direction.

21. The method of claim 19, wherein the one or more structures are not housed in another device during insertion.

22. The method of claim 19, wherein deploying the one or more structures further comprises flexing of the one or more structures relative to the outer surface.

23. The method of claim 22, wherein flexing of the one or more structures occurs about a flexion point formed on the access device.

24. The method of claim 19, wherein deploying the one or more structures further comprises rotating the access device relative to its longitudinal axis in a first direction to deploy the one or more structures into the tissue to prevent movement of the device relative to the body and rotating the access device relative to its longitudinal axis in a second, opposite direction to retract the one or more structures to allow movement of the device relative to the body.

25. The method of claim 19, further comprising decoupling the one or more structures from the body and withdrawing the access device from the body of the patient, the access device translating in a second, opposite direction to the first direction, the one or more structures contacting tissue in the body of the patient during translation of the access device in the second direction.

26. The method of claim 19, wherein the access device is monolithic.

27. A surgical method, comprising:
inserting an access device into a body of a patient, the access device having an inner surface, an outer surface, a proximal end, a distal end, and an opening extending between the proximal and distal ends to receive an instrument therethrough, the access device having one or more structures formed on an outer surface thereof;
translating the access device through the body in a first direction, the one or more structures traveling relative to the body; and
deploying the one or more structures from the outer surface of the access device to couple the one or more structures to the body to increase friction between the one or more structures and the body;
wherein the one or more structures are deployed during translation of the access device through the body in the first direction.

* * * * *